United States Patent [19]
Lamb et al.

[11] Patent Number: 5,082,003
[45] Date of Patent: Jan. 21, 1992

[54] APPARATUS FOR DETERMINING INTERSKELETAL DISTANCES

[75] Inventors: Steve Lamb, Hayward, Calif.; Alan A. Halpern, Kalamazoo, Mich.

[73] Assignee: Orthopedic Systems, Inc., Hayward, Calif.

[21] Appl. No.: 461,180

[22] Filed: Jan. 5, 1990

[51] Int. Cl.$^5$ .............................................. A61B 5/11
[52] U.S. Cl. ........................................ 128/782; 33/512
[58] Field of Search ................. 128/774, 782; 33/511, 33/512; 73/1 E

[56] References Cited

U.S. PATENT DOCUMENTS

| 4,571,834 | 2/1986 | Fraser et al. | 128/782 |
| 4,712,542 | 12/1987 | Daniel et al. | |
| 4,799,497 | 1/1989 | Riley, II | 128/782 |

OTHER PUBLICATIONS

Kinzel et al., Measurement of the Total Motion Between Two Body Segments-1 Analytical Development.

Kinzel et al., Measurement of the Total Motion Between Two Body Segments II Description of Application.

Primary Examiner—Kyle L. Howell
Assistant Examiner—Kevin Pontius
Attorney, Agent, or Firm—Bielen, Peterson & Lampe

[57] ABSTRACT

Apparatus for determining the distance between points on first and second skeletal bodies. The apparatus may continually achieve such distance determination during relative movement between the skeletal bodies. The apparatus includes first and second clamps or aimers each including a tip and base. Aimers are attached to the first and second skeletal bodies and are connected to an articulated linkage. The angular motion of the articulated linkages determines and correlates the movement between first and second aimers attached to the skeletal bodies. The signal produced by the articulated linkage is translated into a measurement of distance between the tips of the first and second skeletal bodies.

17 Claims, 4 Drawing Sheets

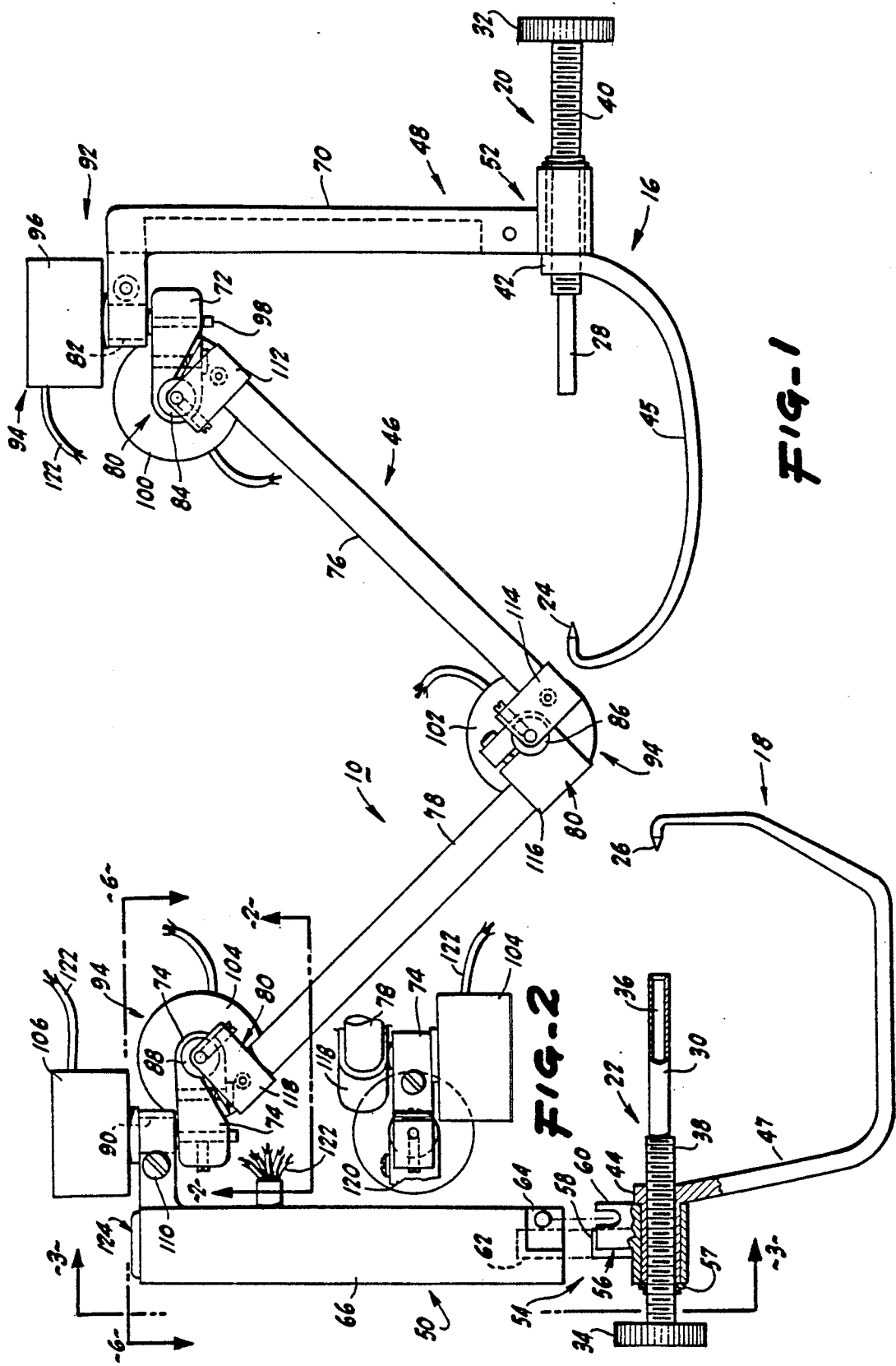

APPARATUS FOR DETERMINING INTERSKELETAL DISTANCES

REFERENCE TO APPENDIX

A computer program is submitted herewith in the form of a microfiche appendix as part of the specification.

BACKGROUND OF THE INVENTION

Present invention relates to an apparatus and method for determining the distance between skeletal bodies moveable relative to one another for the purpose of affecting a ligament graft between the skeletal bodies.

Natural ligaments, when damaged, require replacement through reconstructive surgery. This process often requires replacement of the natural ligament with a grafted ligament.

In the case of the replacement of the anterior or posterior cruciate ligaments of a the knee, it is extremely important to determine the fixation sites for the graft. Such "isometric" positioning of the grafted ligament requires that the sites on the femur and tibia maintain a substantially constant distance from one another during the flexion and extension of the knee.

In the past, tension isometers have been employed in which graft fixation sites are estimated, drilled, pinned, and connected with a tension string. The tension on the string is measured by rotating the knee. If the sites are not correctly initially determined, redrilling and repinning is required. Such process is cumbersome and not very accurate. In this regard, U.S. Pat. No. 4,712,542 describes a method for establishing ligament graft tension and isometry employing a wire cable or suture through the estimated fixation sites on the femur and tibia.

Reference is also made to articles entitled "Measurement of the Total Motion Between To Body Segments I and II" by Kinzel et al, which describes a linkage using a group of links and potentiometers for ascertaining total motion measurements between body segments having six degrees of freedom.

An apparatus method for determining isometric positioning between the femur and tibia for the grafting of cruciate ligaments of the knee would be a noticeable advance in the medical field.

SUMMARY OF THE INVENTION

In accordance with the present invention a novel and useful apparatus for determining the distance between points on a pair of skeletal bodies is herein provided. The apparatus of the present invention utilizes a first and second aimer, clamp, or fixation body. Each aimer may include a tip and a base, and means for attaching the tip and base to the first and second skeletal bodies. Each base of the aimers maybe formed into a tube and may be coaxial with the tip portion of the same. In this regard, the tube maybe used as a guide for drilling an opening though the particular skeletal body. In addition, each aimer may include a curved portion between the tip and base to accommodate the perimeter of the skeletal body to which the aimer is clamped.

The present invention also includes as one of its elements, an articulated linkage having first and second end portions. The first end portion of the articulated linkage is fixed to the first aimer and the second portion of the articulated linkage is fixed to the second aimer. The articulated linkage includes a plurality of links rotatively connected to one another at a plurality of pivots. Electrical potentiometers are found at each pivot and produce an electrical signal indicating the quantity of rotation at each of the pivots. The combined signals generated by such potentiometers maybe translated into a measurement of distance between the first and second skeletal bodies, specifically between the tips of the aimers attached to the first and second skeletal bodies. Such transformation may take place with the aid of a computer and a computer program. Thus, relative movement between the skeletal bodies is accurately and quickly measured. Where isometric fixation points are to be determined in a tibia and femur, the aimers maybe detached and reattached until the distance between the fixation points on such skeletal bodies remains relative constant during full flexion and extension the knee. Specifically, the articulated linkage includes six links and five potentiometers measuring five degrees of freedom. Certain of the potentiometers may lie along parallel axes while others lie along non-parallel axes.

It maybe apparent that a novel and useful apparatus and method for determining the distance between points on first and second skeletal bodies has been described.

It is therefore an object of the present invention to provide apparatus and method which easily and accurately determines the distance between points on first and second skeletal bodies.

It is another object of the present invention to determine the isometric fixation points on a tibia and femur for the purpose of grafting a cruciate ligament therebetween, during reconstructive knee surgery.

A further object of the present invention is to provide an apparatus and method for determining the distance between points on first and second skeletal bodies which eliminates the need for redrilling through the skeletal bodies in the determination of the isometric fixation points on the skeletal bodies.

Yet another object of the present invention is to provide apparatus for determining the distance between points on first and second skeletal bodies which permits easy guiding of a drill to effect the creation of an aperture through the skeletal bodies.

The invention possesses other objects and advantages especially as concerns particular characteristics and features thereof which will become apparent as the specification continues.

BRIEF DESCRIPTION OF THE DRAWINGS

FIG. 1 is a top plan view of the mechanical portion of apparatus of the present invention.

FIG. 2 is a partial bottom plan view taken along line 2—2 of FIG. 1.

Figure 4:
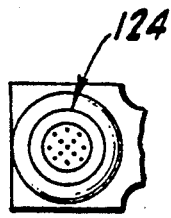
FIG. 4 is a sectional view taken along line 4—4 of FIG. 3.

For a better understanding of the invention reference made to the following detailed description of the preferred embodiments thereof which should be referenced to the hereinabove described drawings.

DETAILED DESCRIPTION OF THE PREFERRED EMBODIMENT

Various aspects of the present invention will evolve from the following detailed description of the preferred embodiments thereof which must be compared to the prior described drawings.

The invention as a whole as shown in the drawings by reference character 10. The apparatus 10 is employed to measure the distance between fixation points on skeletal structures such as femur 12 and tibia 14, shown in FIG. 7. Apparatus 10 includes aimers, clamps, or fixation bodies 16 and 18 as elements thereof. Aimers 16 and 18 include means 20 and 22 for attaching the same to skeletal bodies 12 and 14. It should be noted that means 20 and 22 may take many forms including simple manual holding. In addition, fixation bodies 16 and 18 may also be formed differently than the embodiments illustrated FIG. 1. Aimers 16 and 18, as depicted, include tips 24 and 26 and bases 28 and 30, respectively. Bases 28 and 30 are tubes which extend to knurled knobs 32 and 34. With reference to aimer 18, it maybe seen that tube 30 includes an exemplar bore 36, in this regard. Tubes 28 and 30 are formed with threaded portions 38 and 40, respectively, which threadingly engage threaded bushings 42 and 44. Bushings 42 and 44 extend into generally curved elements 45 and 47 which respectively terminate in tips 24 and 26.

The present invention also includes articulated linkage 46 having first end portion 48 and second end portion 50. Means 52 and 54 is included for fixing aimers 16 and 18, respectively, to first and second end portions 48 and 50 of articulated linkage 46.

Figure 3:
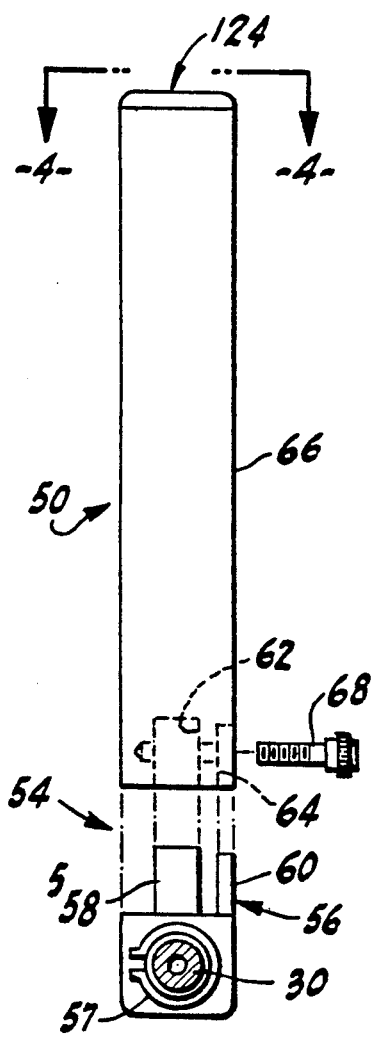
FIG. 3 is a view taken along line 3—3 of FIG. 1.
Figure 5:
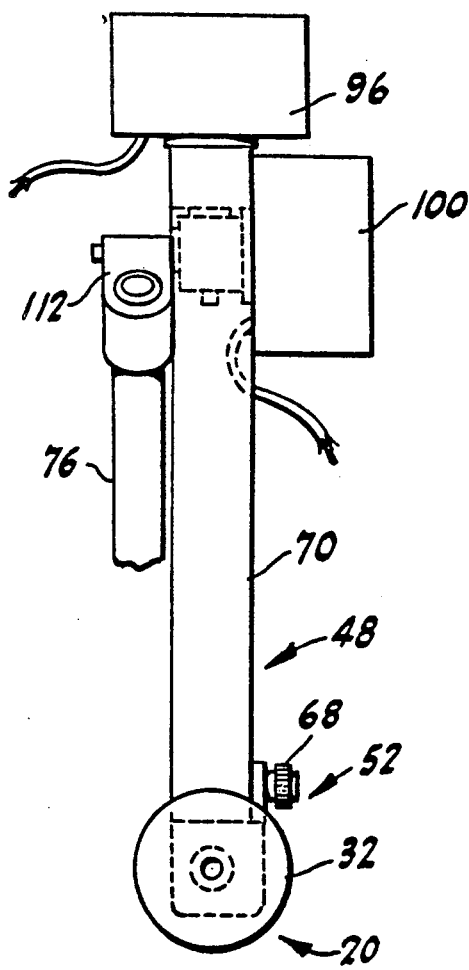
FIG. 5 is a broken right end view of the articulated linkage FIG. 1.

For the sake of clarity, means 54 which is similar to means 52, has been exploded from articulated linkage 46 in FIG. 1. Means 54 includes a block 56 having a tongue 58 and an ear 60, extending therefrom. Tongue 58 and ear 60 fit into recesses 62 and 64 of link 66. Set screw 68 serves as a fastener for means 54, FIG. 3. "C" ring 57 aids in the holding of block 56 in place as shown, FIG. 3.

Articulated linkage 46 is formed from L-shaped first link 70, L-shaped second link 66, third link 72, fourth link 74, fifth link 76, and sixth link 78. Plurality of links 80 of articulated linkage 46 pivotally or rotatively attach to one another by the use of bearings 82, 84, 86, 88, and 90. Each of plurality of links 80 may be constructed of rigid material, such as metal.

Means 92 is also provided for determining angular motion, i.e.: the rotation between adjacent links of plurality of links 80 of articulated linkage 46. Such means 92 includes plurality of potentiometers 94 located at the pivot axes of bearings 82, 84, 86, 88, and 90. Namely, potentiometer 96 measures the relative rotation between first link 70 and third link 72, FIG. 1. A wiper (not shown) within potentiometer 96 changes the value of the voltage applied to potentiometer 96 and transmits an output signal which will be discussed hereinafter. Potentiometer 96 is linked to the shaft 98 of bearing 82 which is connected to the wiper within potentiometer 96. Further, second potentiometer 100 measures the angular rotation between third link 72 and fifth link 76 of articulated linkage 46. Moreover, third potentiometer 102 at the pivot axis of fifth link 76 and sixth link 78, fourth potentiometer 104 at the pivot axis between sixth link 78 and fourth link 74, and fifth potentiometer 106 at the pivot axis between second link 66 and fourth link 74, serve the same purpose as potentiometer 96 and are construct similarly to the first potentiometer 96 at the rotational axis of first link 70 and third link 72. Plurality of potentiometers 94 each may be an Econopot Mark 5 manufactured by New England Instruments, of Natik, Mass.

Figure 6:
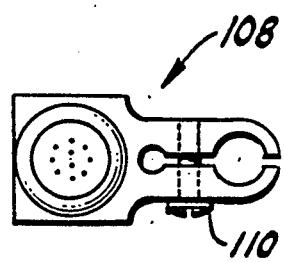
FIG. 6 is a sectional view taken along line 6—6 of FIG. 1.

Bearings 84, 86, 88, and 90 are clamped in place between plurality of links 80 by exemplar clamp 108, FIG. 6, utilizing set screw 110. Clamps 112, 114, 116, 118, and 120, perform a similar function with the remaining plurality of links 80. Lead wires 122, each containing a pair of conductors, are routed from first link 66 to plurality of potentiometers 94. A quick connector 124, FIG. 4, serves as a terminus for the imputed voltage (approximately 15 voltage DC) and the output signals of plurality of potentiometers 94.

Figure 7:
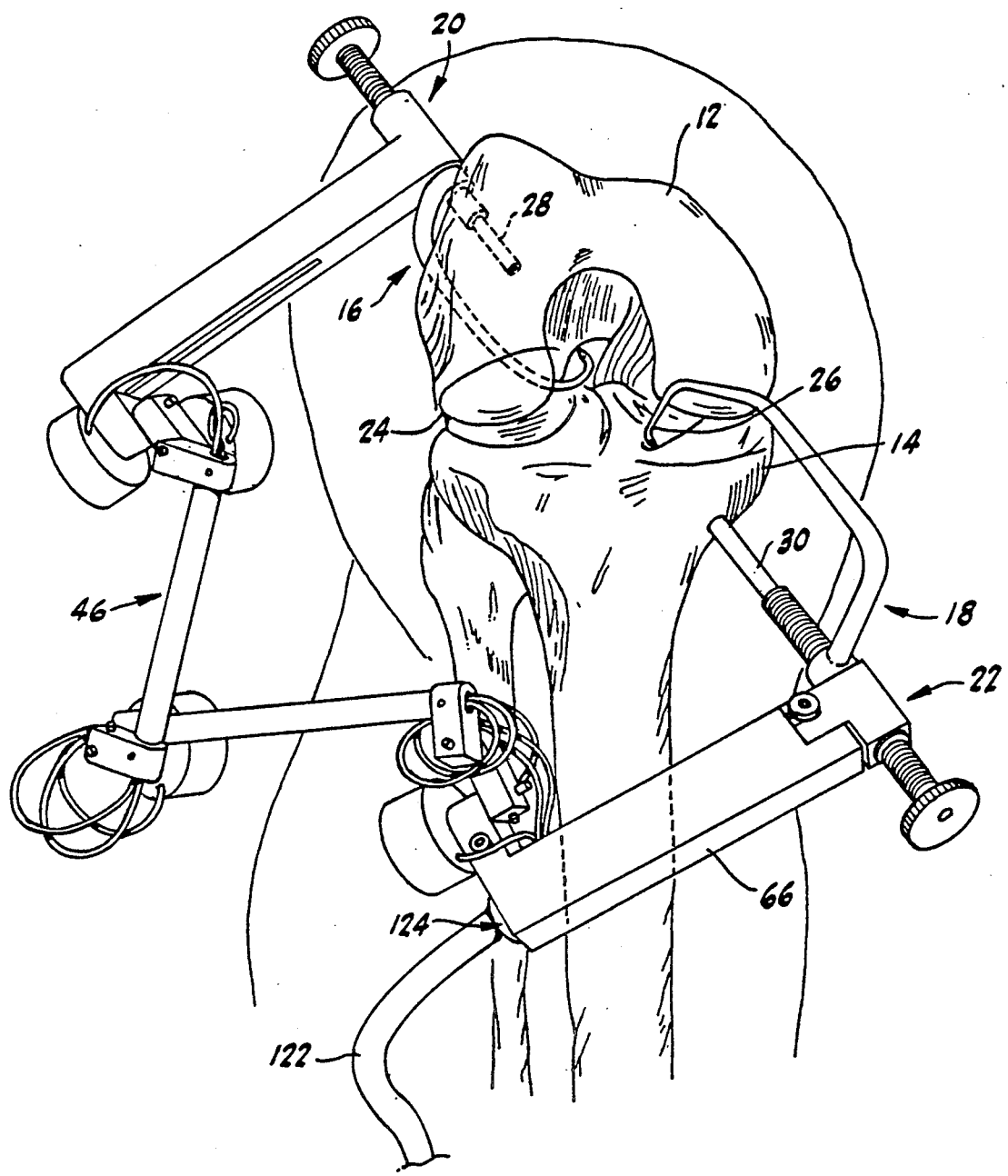
FIG. 7 is a isometric view showing the apparatus of the present invention in place relative to a knee joint prepared for reconstructive surgery.
Figure 8:
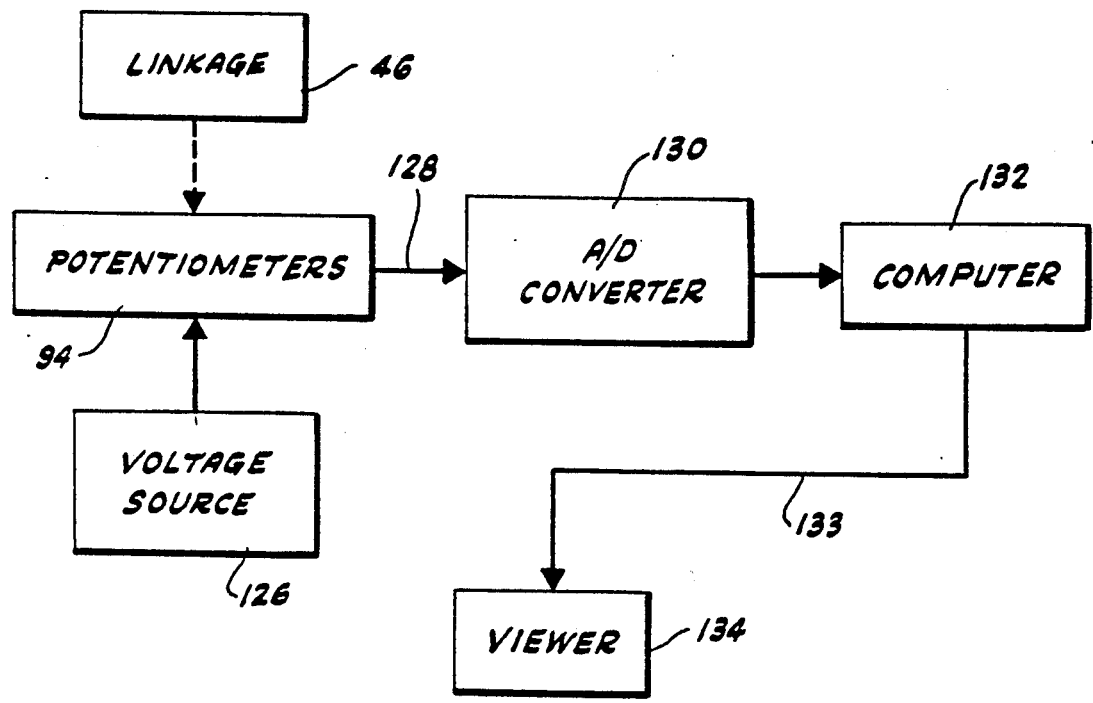
FIG. 8 is a block diagram depicting the schematic processing of the signals from the plurality of potentiometers of the present invention.
Figure 9:
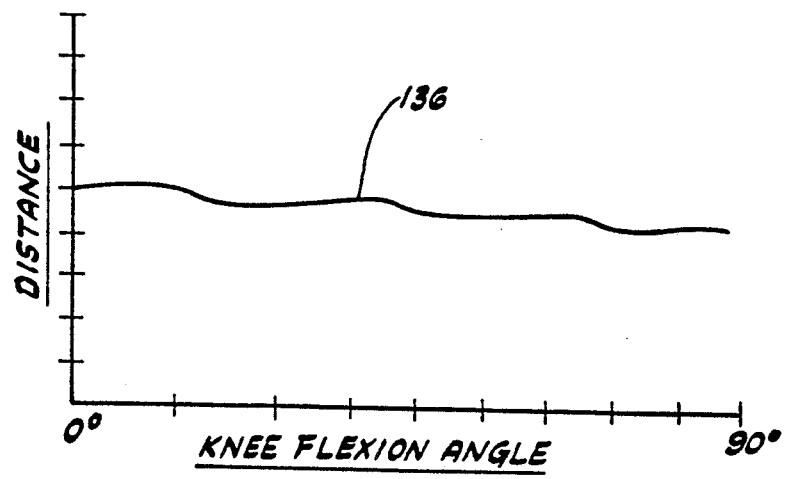
FIG. 9 is a graphical display of the change in distance between the aimer tips during the flexion of the knee depicted in FIG. 7 from 0 to 90 degrees.

With reference to FIG. 8, it may be observed that a source of voltage 126 feeds plurality of potentiometers 94. Mechanical signals from articulated linkage 46 is also fed into the plurality of potentiometers 94 to indicate the rotational motion of each of the pivot axes therefore, described as lying between plurality of links 80. Output signals 128 in the form of five distinct voltages, one from each potentiometer, pass to an analog to digital converter 130. A computer 132, such as a Datavue computer Model Snap 1+1, manufactured by Datavue of Norcross Ga., processes the data signal 133 and sends the same to a printer or viewer 134 by means of an appropriate computer program, submitted herewith as an appendix. A typical graph, FIG. 9, shows the distance between tips 24 and 26 of aimers 16 and 18 plotted as a function the knee flexion angle between tibia 14 and femur 12, FIG. 7. The computer 132, the computer program and the viewer 134, provide a means for selectively repositioning said first and second aimers to minimize the change of distance between the tips during movement of the first and second skeletal bodies.

In operation, apparatus 10 maybe used for reconstructive knee surgery, as shown in FIG. 7, i.e. the replacement of the anterior cruciate ligament. In this regard, the surgical preparation of the knee is well know and discussed in U.S. Pat. No. 4,712,542. FIG. 7 represent initial placement of apparatus 10 in which aimer 16 has been attached to the patient's femur 12 and aimer 18 has been attached to the patients tibia 14. Tips 24 and 26 are initially placed as depicted in FIG. 7 and clamped into place using means 20 and 22. Articulated linkage 46, having five degrees of freedom, bridges aimer 16 and 18 and quintet of wires 122 are lead to the pertinent electrical components, shown on FIG. 8, via connector 124. Since isometric placement is essential in proper grafting of a new ligament in place of the natural anterior cruciate ligament, the knee is flexed from 0 to 90 degrees, FIG. 9. The relative distances between tips 24 and 26 are continually measured during this flexion by the program accompanying computer 132 and are displayed or printed out on viewer 134. It has been found that a change in the distance between tips 24 and 26 of 2 millimeters or less represents an acceptable placement of tips 24 and 26. In this regard, graph line 136, FIG. 9 shows a satisfactory result. If the distance between tips 24 and 26 is unsatisfactory the aimers may be moved relative to one another, again the computer program suggests the direction of such move. It is preferred, however that the tibia aimer 18 remain fixed while the femoral aimer 16 be moved to improve the isometery between aimer tips 24 and 26. It should be noted that once isometric placement of tips 24 and 26 has been achieved, base tubes 28 and 30 maybe used as a guide for a bone drill, such as a "K wire". The grafted ligament would generally be attached where the ends of base tubes 28 and 30 touch femur 12 and tibia 14.

While in the foregoing embodiments of the present invention have been set forth in considerable detail for the purposes of making a complete disclosure of the invention, it may be apparent to those of skill in the art that numerous changes may be made in such details without departing from the spirit and principles of the invention.

What is claimed is:

1. An apparatus for determining the distance between points on first and second skeletal bodies during movement of the first and second skeletal bodies relative to one another, comprising:
    a. a first aimer including a first tip and a first base, said first aimer including means for attaching the first tip and first base to the first skeletal body, said first base of said first aimer including a first tube permitting access to the first skeletal body;
    b. a second aimer including a second tip and a second base, said second aimer including means for attaching the second tip and second base to the second skeletal body, said second base of said second aimer including a second tube permitting access to the second skeletal body;
    c. an articulated linkage having a first end portion and a second end portion, said first end portion of said articulated linkage being fixed to said first aimer, said second end portion of said articulated linkage being fixed to said second aimer;
    d. means for determining angular motion in said articulated linkage correlated to movement between said first and second tips attached to the first and second skeletal bodies; and
    e. means for transforming said articulated linkage angular motion into a measurement of distance between said first and second skeletal bodies.

2. The apparatus of claim 1 in which said articulated linkage includes a plurality of links rotatively connected to one another at a plurality of pivots, and a plurality of electrical potentiometers located at each of said plurality of pivots.

3. The apparatus of claim 2 in which at least two of said plurality of potentiometers pivot on separate axes.

4. The apparatus of claim 3 which additionally comprises means for obtaining an electrical signal from each of said plurality of potentiometers and producing a graphical representation of said movement between said first and second tips.

5. The apparatus of claim 3 in which said means for transforming said angular motion in said articulated linkage includes a computer and a computer program.

6. The apparatus of claim 2 in which said articulated linkage includes a first link fixed to said first aimer, a second link fixed to said second aimer, a third link pivotally attached to said first link, a fourth link pivotally attached to said second link, a fifth link pivotally attached to said third link, and a sixth link pivotally attached to said, fourth and fifth links.

7. The apparatus of claim 6 in which said means for determining angular motion in said articulated linkage includes a first potentiometer measuring pivotal motion between said first and third links, a second potentiometer for measuring pivotal motion between said third and fifth links, a third potentiometer for measuring pivotal motion between said fifth and sixth links, a fourth potentiometer for measuring pivotal motion between said fourth and sixth links, and a fifth potentiometer for measuring pivotal motion between said second and fourth links.

8. The apparatus of claim 7 in which said first and fifth potentiometers pivot on parallel axes.

9. The apparatus of claim 7 in which said second, third, and fourth potentiometers pivot on parallel axes.

10. The apparatus of claim 1 in which said first tube and said first tip lie along one common axis and said second tube and said second tip lie along another common axis.

11. The apparatus of claim 1 in which said first and second aimers each include a curved portion between said first tip and said first base, and said second tip and said second base.

12. A method of determining the distance between points on first and second skeletal bodies during movement of the first and second skeletal bodies relative to one another, comprising the steps of:
    a. attaching a first aimer having a first tip and a first base to the first skeletal body;
    b. attaching a second aimer having a second tip and a second base to the second skeletal body;
    c. fixing an articulated linkage having first and second end portions to said first and second aimers;
    d. determining the angular motion in said articulated linkage correlated to movement between said first and second tips attached to said first and second skeletal bodies;
    e. transforming said, angular motion in said articulated linkage into a measurement of movement between said first and second tips;
    f. selectively repositioning said first and second aimers to minimize the change of distance between the tips during movement of the first and second skeletal bodies.

13. An apparatus for determining isometric positioning between first and second skeletal bodies during movement of the first and second skeletal bodies relative to one another, comprising:
    a. a first aimer including a first tip and a first base, said first aimer including means for attaching the first tip and first base to the first skeletal body;
    b. a second aimer including a second tip and a second base, said second aimer including means for attaching the second tip and second base to the second skeletal body;
    c. an articulated linkage having a first end portion and a second end portion, said first end portion of said articulated linkage being fixed to said first aimer, said second end portion of said articulated linkage being fixed to said second aimer;
    d. means for determining angular motion in said articulated linkage correlated to movement between said, first and second tips attached to said first and second skeletal bodies;
    e. means for transforming said articulated linkage angular motion into a measurement of distance between said first and second skeletal bodies; and means for selectively repositioning said first and second aimers to minimize the change of distance between the tips during movement of the first and second skeletal bodies.

14. The apparatus of claim 13 in which said articulated linkage includes a plurality of links rotatively connected to one another at a plurality of pivots, and a plurality of electrical potentiometers located at each of said plurality of pivots.

15. The apparatus of claim 14 in which at least two of said plurality of potentiometers pivot on separate axes.

16. The apparatus of claim 15 which additionally comprises means for obtaining an electrical signal from each of said plurality of potentiometers and producing a graphical representation of said movement between said first and second tips.

17. The apparatus of claim 15 in which said means for transforming said angular motion in said articulated linkage includes a computer and a computer program.

* * * * *